(12) United States Patent
Ujhelyi et al.

(10) Patent No.: US 7,722,598 B2
(45) Date of Patent: May 25, 2010

(54) APPARATUS AND SYSTEM FOR DELIVERY OF DRUG THERAPIES

(75) Inventors: Michael R. Ujhelyi, Maple Grove, MN (US); Rahul Mehra, Stillwater, MN (US); Xiaoyi Min, Thousand Oaks, CA (US)

(73) Assignee: Medtronic, Inc., Minneapolis, MN (US)

( * ) Notice: Subject to any disclaimer, the term of this patent is extended or adjusted under 35 U.S.C. 154(b) by 426 days.

(21) Appl. No.: 11/675,693

(22) Filed: Feb. 16, 2007

(65) Prior Publication Data

US 2007/0203473 A1  Aug. 30, 2007

Related U.S. Application Data

(62) Division of application No. 10/407,996, filed on Apr. 4, 2003, now Pat. No. 7,186,247.

(51) Int. Cl.
*A61K 9/22* (2006.01)
(52) U.S. Cl. ..................... 604/890.1; 604/67
(58) Field of Classification Search .......... 604/890.1, 604/891.1, 65–67, 288.03
See application file for complete search history.

(56) References Cited

U.S. PATENT DOCUMENTS

| | | | |
|---|---|---|---|
| 4,645,489 A | 2/1987 | Krumme et al. | |
| 4,871,351 A | 10/1989 | Feingold | |
| 5,041,107 A | 8/1991 | Heil | |
| 5,170,801 A * | 12/1992 | Casper et al. | 600/582 |
| 5,387,419 A | 2/1995 | Levy et al. | |
| 5,458,631 A | 10/1995 | Xavier | |
| 5,554,119 A | 9/1996 | Harrison et al. | |
| 5,820,589 A | 10/1998 | Torgerson et al. | |
| 5,865,787 A | 2/1999 | Shapland et al. | |
| 5,893,881 A | 4/1999 | Elsberry et al. | |
| 6,048,328 A * | 4/2000 | Haller et al. | 604/288.03 |
| 6,086,582 A | 7/2000 | Altman et al. | |
| 6,102,887 A | 8/2000 | Altman | |
| 6,355,014 B1 | 3/2002 | Zadno-Azizi et al. | |
| 6,488,652 B1 | 12/2002 | Weijand et al. | |

(Continued)

FOREIGN PATENT DOCUMENTS

EP  1293808 B1  5/2006

(Continued)

OTHER PUBLICATIONS

Labhasetwar, V., et al., "Prevention of Acute Inducible Atrial Flutter in Dogs by Using an Ibutilide-Polymer-Coated Pacing Electrode", J Cardiovasc Pharmacol, vol. 31(3), Mar. 1998, pp. 449-455.

*Primary Examiner*—Nicholas D Lucchesi
*Assistant Examiner*—Theodore J Stigell
(74) *Attorney, Agent, or Firm*—Michael C. Soldner

(57) ABSTRACT

A medical delivery system for delivering a fluid to a desired location within a body that includes a first member having an aperture, and a second member adapted to be positioned over the first member. The fluid to be delivered is contained within a fluid storage device, formed by at least one of the first member and the second member. The medical delivery system includes means for repositioning the first member relative to the second member between a first state preventing passage of the fluid through the aperture and a second state enabling passage of the fluid outward from the fluid storage device through the aperture.

22 Claims, 2 Drawing Sheets

U.S. PATENT DOCUMENTS

| | | |
|---|---|---|
| 6,520,477 B2 | 2/2003 | Trimmer |
| 6,705,585 B1 | 3/2004 | Roy |
| 6,723,072 B2 | 4/2004 | Flaherty et al. |
| 6,916,159 B2 | 7/2005 | Rush et al. |
| 6,926,246 B2 | 8/2005 | Ginggen |
| 6,979,315 B2 | 12/2005 | Rogers et al. |
| 7,186,247 B2 * | 3/2007 | Ujhelyi et al. ........... 604/891.1 |
| 2002/0013557 A1 * | 1/2002 | Sherry .................. 604/288.03 |

FOREIGN PATENT DOCUMENTS

| | | |
|---|---|---|
| WO | WO0048533 A1 | 8/2000 |
| WO | WO01/41846 | 6/2001 |
| WO | WO01/56633 | 8/2001 |
| WO | WO0156633 A2 | 8/2001 |
| WO | WO0166173 A1 | 9/2001 |

* cited by examiner

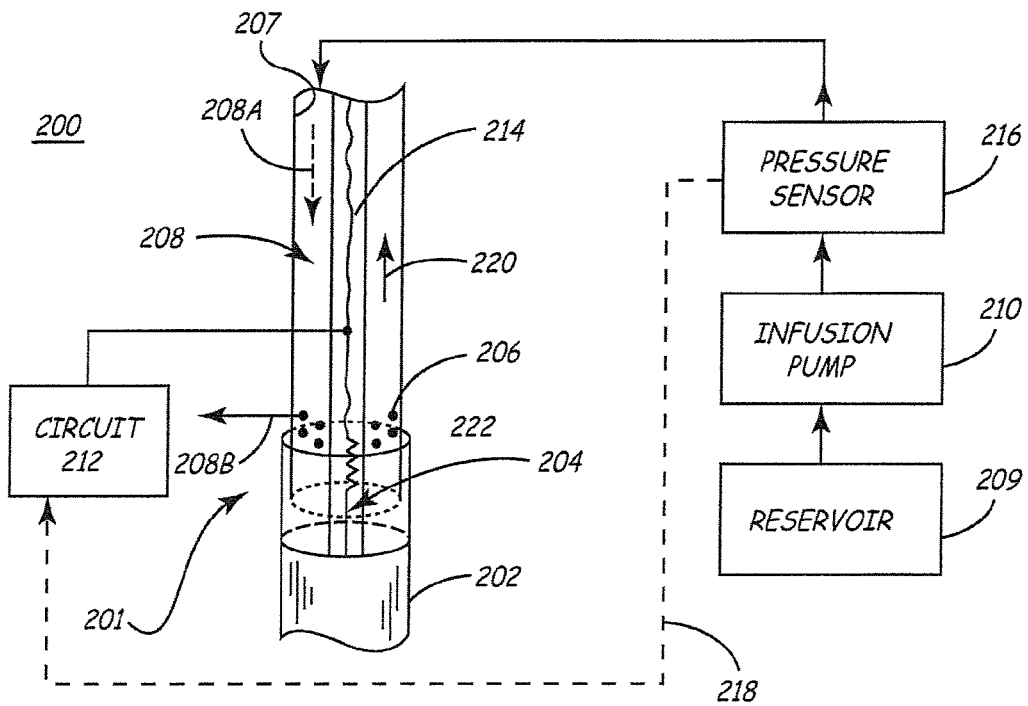
FIG. 2
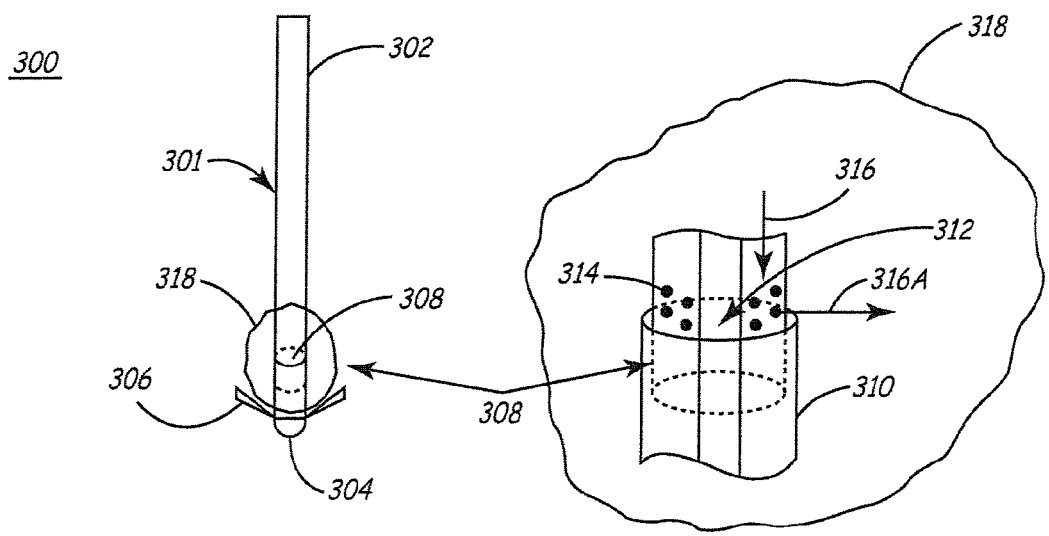
FIG. 3A
FIG. 3B

APPARATUS AND SYSTEM FOR DELIVERY OF DRUG THERAPIES

CROSS-REFERENCE TO RELATED APPLICATION

This is a divisional application of and claims priority to U.S. Ser. No. 10/407,996 filed Apr. 4, 2003 now U.S. Pat. No. 7,186,247, entitled 'APPARATUS AND SYSTEM FOR DELIVERY OF DRUG THERAPIES", incorporated herein by reference in its entirety.

FIELD OF THE INVENTION

The present invention generally relates to delivering a drug to an internal body tissue, and in particular, the present invention relates to an apparatus and system that provides improved control of drug delivery to an internal body tissue.

BACKGROUND OF THE INVENTION

Drug therapies are a primary component of an overall patient health plan. Drugs or therapeutic agents can be delivered to a patient in various ways including oral ingestion, intramuscular and/or intravenous injection or topical absorption. Most of these approaches require administration by medical professionals or regular patient compliance with the drug regimen. In addition, these drug delivery approaches, although useful, are not very effective in delivering therapeutic agents to internal body tissues or organs.

Drugs and therapeutic agents can also be administered through the use of catheters. Catheters are medical devices designed for insertion into a body passageway that facilitate injection or withdrawal of fluids into a patient's body. Catheters provide an advantage of direct vascular and/or local delivery of a therapeutic agent to body tissues and organs that can include the heart, esophagus, stomach, large intestine, and other tissues which may be accessed via a catheter system. Catheters and catheter systems can deliver drugs to the sites where they are most needed, reduce the amount of medication required, and improve the control over the time for delivering the drug. However, drug deliver using current drug delivery devices can be problematic in that certain problems, such as the growth of tissue over the catheter opening, control of the fluid flow rate of the drug being administered, and resistance from other bodily fluids when introducing the drug need to be addressed.

One approach to overcoming some of these drawbacks is to use an implantable infusion pump. Implanted infusion pumps usually include a pressurized drug reservoir and a form of fluid flow control. However, for some applications, implantable infusion pumps are inadequate because the amount of the therapeutic agent required for delivery and the need for additional pressure exceed the capability of most infusion pumps. Redesigning the infusion pump to address these deficiencies substantially increases the cost and size of the device.

There is a need for a drug delivery system for administering drug therapies that can be used with conventional, implantable infusion pumps and catheters, and that addresses the aforementioned problems, as well as other related problems.

SUMMARY OF THE INVENTION

Various embodiments of the present invention are directed to addressing the above and other needs in connection with vascular and/or local drug delivery arrangements that improve the performance of implantable fusion pumps, catheter systems and other drug delivery devices.

According to an embodiment of the present invention, a medical delivery system for delivering a fluid to a desired location within a body includes a first member having an aperture and a second member adapted to be positioned over the first member. The fluid is contained within a fluid storage device, formed by at least one of the first member and the second member. The system includes means for repositioning the first member relative to the second member between a first state preventing passage of the fluid through the aperture and a second state enabling passage of the fluid outward from the fluid storage device through the aperture.

According to another embodiment of the present invention, a medical delivery system for delivering a fluid to a desired location within a body includes a first member having an aperture and a second member adapted to be positioned over the first member. The fluid is contained within a fluid storage device, formed by at least one of the first member and the second member. The system includes means for repositioning the first member relative to the second member between a first state preventing passage of the fluid through the aperture and a second state enabling passage of the fluid outward from the fluid storage device through the aperture. A pressure sensing device is communicatively coupled to the repositioning means, and is adapted to sense pressure and generate a pressure feedback signal, wherein the repositioning means repositions the first member relative to the second member in response to the pressure feedback signal.

The above summary of the present invention is not intended to describe each illustrated embodiment or every implementation of the present invention. The figures in the detailed description that follow more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIG. 2 illustrates a drug delivery system according to another example embodiment of the invention;

FIG. 3A illustrates another drug delivery arrangement according to another example embodiment of the invention; and FIG. 3B illustrates an exploded view of a drug delivery device of the arrangement of FIG. 3A according to another example embodiment of the invention.

Figure 1:
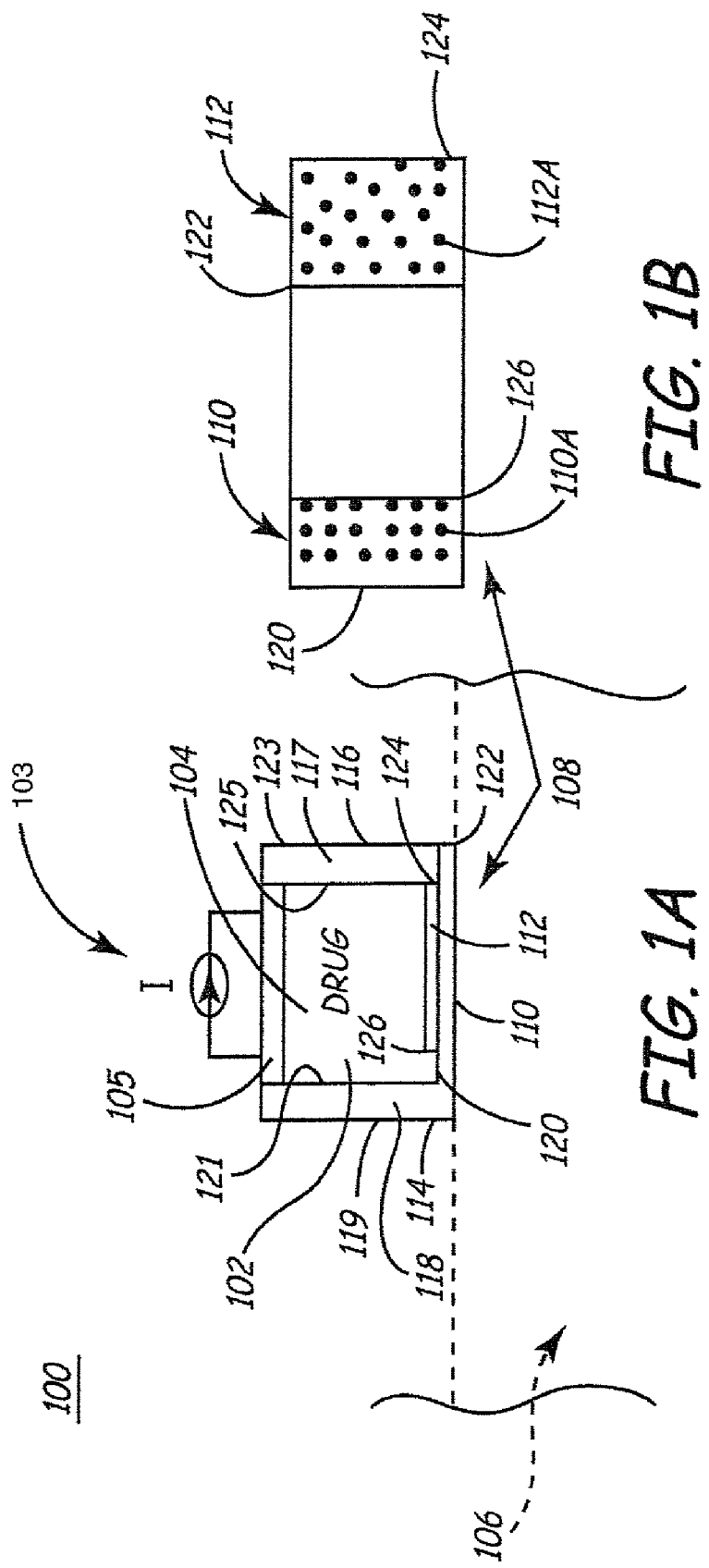
FIG. 1A illustrates a drug delivery arrangement according to an example embodiment of the invention.
FIG. 1B illustrates a wall portion of the drug delivery arrangement of FIG. 1A according to an example embodiment of the invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

The present invention is generally directed to a drug delivery arrangement that improves the performance of implantable fusion pumps, catheter systems and other drug delivery devices. In one example embodiment, the present invention prevents blood coagulation at a distal end of a drug delivery system by preventing the blood from flowing back into the tubing of the drug delivery system. In an example application, the present invention facilitates the treatment of atrial fibrillation and atrial flutter through pharmaceutical therapies, as an alternative to electrical cardioversion therapy. While the present invention is not necessarily limited to such an application, the invention will be better appreciated using a discussion of example embodiments in such a specific context.

According to an embodiment of the present invention, an implantable drug delivery device includes a drug reservoir having movable surfaces or plates at a drug delivery end or wall portion. The movable plates have two surfaces overlapping each other when the drug delivery device is in an OFF state, so that, while in the OFF state, the drug remains inside the drug reservoir. However, when in an ON state, the drug is able to flow out of the reservoir in a controllable displacement or flow via apertures disposed in the movable plates that become exposed in response to relative movement of the movable surfaces. The motion of the movable plates results from elongation of the plate material upon receiving heat generated from an electrical source (current or voltage), a magnetic source or a thermal source. The plate material includes shape memory alloys responsive to various external stimuli. The shape memory alloy used is configurable to include apertures that open and close as the material elongates and contracts in response to the external stimulation, as described below.

FIG. 1A illustrates a drug delivery device according to an illustrative embodiment of the present invention. As illustrated in FIG. 1A, a drug delivery device 100 according the present invention delivers a drug 102 stored within a drug reservoir 104 to an internal body tissue or organ 106 through apertures of a bottom side 108 of the drug delivery device 100. The drug delivery device 100 includes a top side 105, along with a first wall member 114 and a second wall member 116 that form the drug reservoir 104. In particular, first wall member 114 includes a first side wall 118 integral with a first plate 110 that extends the entire length of bottom side 108 when drug delivery device is in an OFF state, illustrated in FIG. 1A. Second wall member 116 includes a second side wall 117 integral with a second plate 112 having a length shorter than first plate 110 and slideably positioned over first plate 110. First side wall 118 extends horizontally between an outer side 119 and an inner side 121 and second side wall 117 extends horizontally between an outer side 123 and an inner side 125.

The drug delivery device 100 is located proximate to body tissue 106 to maximize drug delivery through the bottom side 108 of drug delivery device 100. Drug 102 is released through bottom side 108 and into body tissue 106 upon receipt of an external stimulus at wall member 114 and wall member 116. In this example, an electrical circuit 103, located external to or within drug delivery device 100, such as a pump system, or within an implantable pulse generator, such as a pacemaker, cardiac defibrillator/cardioverter, provides the external stimulus to wall member 114 and wall member 116. The external stimulus, which can either be electrical, magnetic or thermal, physically reconfigures the relative position of first plate 110 and second plate 112 forming bottom side 108 so that drug 102 is released through bottom side 108 and into body tissue or organ 106, as described below.

FIG. 1B illustrates a detailed view of a bottom side of the drug delivery device of FIG. 1A according to an illustrative embodiment of the invention. As illustrated in FIG. 1B, bottom side 108 is formed by overlapping plates 110 and 112 made of a shape memory alloy, with plate 110 extending from a first end 120, at which a series of one or more apertures 110A are positioned, to a second end 122, and plate 112 extending from a first end 124, at which a series of one or more apertures 112A are positioned, to a second end 126.

According to the present invention, when the drug delivery device is in an OFF state, plates 110 and 112 are relatively positioned so that plate 112 is positioned over apertures 110A so that drug is prevented from passing through bottom side 108 via apertures 110A of plate 110, and plate 110 is positioned over apertures 112A so that drug is prevented from passing through bottom side 108 via apertures 112A of plate 112. On the other hand, apertures 110A and 112A of plates 110 and 112, respectively, allow drug 102 of FIG. 1A to flow outward from drug reservoir 104 to body tissue 106 when plates 110 and 112 are positioned in an ON state, illustrated in FIG. 1B. In particular, when plates 110 and 112 are positioned in the OFF state, second end 126 of plate 112 is positioned to cover apertures 110A of plate 110 and second end 122 of plate 110 is positioned to cover apertures 112A of plate 112 to prevent flow of drug 102 outward from drug reservoir 104. As wall members 114 and 116 are electrically stimulated by circuit 103, plates 110 and 112 begin to elongate and expose apertures 110A and 112A such that drug 102 is released through one or more of apertures 110A and 112A into body tissue 106 of FIG. 1A. The relative movement of plates 110 and 112 results from elongation of the plate material upon receiving heat generated from an electrical source (current or voltage). In this example embodiment, the plates are made from a Nitinol-based shape memory alloy that is a 50/50 mix of titanium nitinol, for example.

The choice of the type of shape memory alloy used in the various embodiments of bottom portion 108 depends on where the movable plate arrangement will be used and the acceptable range of electrical, thermal or magnetic parameters. The distribution and size of the apertures in the movable plates are designed according to particular parameters for the flow rate and drug dosage requirements of an individual patient or condition to be treated. The quantity of displacement of the movable plates can be controlled by the source providing the stimulus to the plates.

According to an embodiment of the present invention, apertures 110A and 112A may be positioned so as to be offset relative to each other in such a way as to minimize the distance that plates 110 and 112 are required to advance relative to each other in order to enable drug 102 to flow outward from drug reservoir 104.

It is understood that while the drug delivery device 100 described in reference to FIGS. 1A and 1B includes one or more apertures 110A and 112A located along both plates 110 and 112, the present invention is intended to include other combinations of apertures and movable plates. For example, according to an alternate embodiment of the present invention, one or more apertures are positioned along only one of plates 110 and 112, and/or only one of plates 110 and 112 moves in response to the electrical stimulation from circuit 103. According to yet another embodiment of the present invention, apertures are included only along first plate 110, and are in direct opposition to second plate 112 when delivery device 100 is in the closed state preventing flow of drug 102 from drug reservoir 104. The external stimulus is received at plate 110 and top side 105, so that only top side 105 and plate 110 are physically reconfigured, while second plate 112 remains at a fixed position. When top side 105 and plate 110 expand, the apertures positioned along plate 110 move relative to fixed plate 112 to become exposed, enabling flow of drug 102 through the apertures. The magnitude of the physical reconfiguration of plate 110 is controlled via pressure feedback to meet a desired flow rate.

FIG. 2 illustrates a drug delivery system according to an alternate embodiment of the present invention. As illustrated in FIG. 2, a drug delivery system 200 according to an alternate embodiment of the present invention includes a valve arrangement 201 for connecting to an implantable infusion pump 210. Valve 201 includes an outer sleeve member 202 and an inner sleeve member 204, having a diameter less than the outer sleeve member 202 so as to be insertable within the outer sleeve member 202, with one or more apertures 206 positioned along inner sleeve member 204. A medicinal fluid 208 flows within an interior 207 of inner sleeve 204, in the direction of dashed arrow 208A. When in an OFF state, inner sleeve member 204 is positioned relative to outer sleeve member 202 so that apertures 206 are covered by outer sleeve member 202, preventing fluid 208 from exiting from inner sleeve member 204 via apertures 206.

On the other hand, when in an ON state, inner sleeve member 204 is positioned relative to outer sleeve member 202 so that apertures 206 are not covered by outer sleeve member 202, enabling fluid 208 to exit from inner sleeve member 204 via apertures 206. Fluid 208 exits inner sleeve 204 through apertures 206, as indicated by directional arrow 208B, flowing into a patient. Fluid 208 is pumped out of a drug reservoir 209 by infusion pump 210, infusion pump 210 drawing suction from reservoir 209 and discharging into inner sleeve 204.

Medicinal fluid 208 flows to the patient after valve 201 opens as a result of stimulating inner sleeve member 204. In one example implementation, inner sleeve member 204 is stimulated directly with an electrical current from a wire 214 disposed within sleeve member 204 provided by an electrical circuit 212. The electrical stimulation of inner sleeve member 204 causes inner sleeve member 204 to elongate and expose apertures 206 thereby allowing medicinal fluid 208 to flow to the patient. Inner sleeve member 204 elongation results in relative motion of portions of inner sleeve member 204 with respect to outer sleeve member 202, as indicated by directional arrow 220. In another example implementation, an electrical current through wire 214 indirectly stimulates inner sleeve member 204, the electrical current causing a heating element 222 to generate heat, and the heat causing member 204 to elongate, and expose apertures 206.

Medicinal fluid flow can cease before infusion pump 210 stops by closing valve 201 via a reconfiguration of inner sleeve member 204, for example by stimulating member 204 using reverse polarity current, or by curtailing electrical current flow thereby cooling heating element 222 respectively. This approach allows better control of the flow rate of the medicinal fluid stream through the apertures. Providing movable surfaces in valve 201 for use with infusion pump 210 improves drug flow and pump efficiency. For a more detailed discussion of implantable infusion pumps, reference is made to U.S. Pat. No. 5,820,589 to Torgerson, et al., which is assigned to the assignee of the present invention and is incorporated herein by reference in its entirety.

The present invention addresses certain difficulties that currently exist in known valve designs, such as controlling the flow rate of the medicinal fluid, high resistance from the surrounding blood or bodily fluids to introduction of the drug, and limited pressure generated from the infusion pump 210. In particular, the present invention utilizes the reconfiguration properties of the shape memory alloy in inner sleeve member 204 so that the internal pressure generated by infusion pump 210 enables medicinal fluid 208 to flow outside valve 201 more easily when the valve 201 is open, and will prevent blood from refluxing into apertures 206. System 200 has low resistance, and the pressure generated from infusion pump 210 only needs to be slightly greater than that of the blood or surrounding bodily fluid to move medicinal fluid 208 out of valve 201. Once the fluid 208 is delivered, valve 201 is closed completely with an additional electrical stimulus. The drug flow rate from valve 201 can be more easily controlled by infusion pump 210, circuit 212, and the design of inner sleeve member 204 according to the present invention. The present invention improves the control of fully turning ON or OFF valve 201 to prevent drug leakage. The drug dosage and speed of delivery is also controlled more precisely.

According to a further example embodiment of the present invention, fluid 208 is pumped out of a drug reservoir 209 by infusion pump 210, pump 210 drawing suction from reservoir 209 and discharging fluid 208 into inner sleeve 204 through pressure sensor 216. Pressure sensor 216 detects pressure of the flow of medicinal fluid 208 at a selected location between infusion pump 210 and a point at which the medicinal fluid 208 exits through apertures 206. As discussed above, the elongation of inner member 204, and the relative movement of portions of member 204 with respect to outer member 202, is proportional to the amount of stimulation experienced by member 204. Therefore, the quantity of apertures 206 exposed through which fluid can flow, the flow rate and pressure of medicinal fluid through apertures 206, are also controlled by the amount of stimulation experienced by member 204. As more apertures are exposed, pump 210 backpressure decreases and flow rate increases, but at a lower fluid pressure as sensed by pressure sensor 216. The rate and pressure of fluid delivery to the patient is thereby proportional to the stimulation to inner member 204.

In order for medicinal fluid to exit apertures 206, the pressure of fluid flow through apertures 206 must be greater than a predetermined threshold, such as the patient's blood pressure for example. If medicinal fluid pressure is too low, bodily fluid will flow into the interior of inner member through exposed apertures 206. Unnecessarily exposing too many apertures 206 reduces medicinal fluid delivery pressure. Additionally, exposing apertures 206 to bodily fluids (e.g., blood cells and proteins) subjects the apertures to buildup of blockage elements. Conversely, an excessive medicinal fluid pressure through apertures 206 resulting from exposing too few apertures, may be detrimental to pump 210, and/or the patient.

According to one aspect, stimulation of inner member 204 is controlled to limit the quantity of exposed apertures 206, while providing medicinal fluid flow through the apertures 206 at a pressure not to exceed a selected maximum threshold. A closed loop feedback path 218 communicatively couples pressure sensor 216 with the inner sleeve elongation control mechanism, circuit 212 for example. As pressure increases, and is detected by sensor 216, sensor 216 electrically communicates a feedback signal to circuit 212 via feedback path 218. Circuit 212 stimulates inner sleeve 204 responsive to the feedback signal thereby causing additional apertures 206 to be exposed and mitigating the detected pressure increase. The quantity of exposed apertures is controlled to maintain fluid pressure according to a selected flow rate, not to exceed a selected maximum pressure, 250 mm Hg for example. For example, the inner sleeve member 204 is initially stimulated to cause a limited number of apertures 206 to be exposed. If fluid pressure is subsequently sensed to be too high, a pressure feedback signal causes further stimulation of inner sleeve member 204 resulting in more of apertures 206 to be exposed.

FIG. 3A illustrates a drug delivery system 300 that includes a drug delivery device 308 according to another example embodiment of the invention. In particular, drug delivery system 300 includes a catheter 301 having a catheter body 302 and a catheter tip 304 with a pair of tines 306 for anchoring catheter 301 to body tissue. Drug delivery system 300 further includes drug delivery device 308 that is mounted between catheter body 302 and catheter tip 304 for local delivery of medication. The medication can be in the form of a fluid or a solid that can travel within catheter 301.

FIG. 3B illustrates an exploded view of drug delivery device 308 of FIG. 3A according to another example embodiment of the invention. Drug delivery device 308 includes an outer sleeve member 310 and an inner sleeve member 312 having a plurality of apertures 314. A drug 316 elutes out of inner sleeve member 312 via apertures 314 once drug delivery device 308 is in an ON position in response to an electrical stimulation of inner sleeve member 312. In the ON state, the electrical stimulation of inner sleeve member 312 causes inner sleeve member 312 to elongate and expose apertures 314, thereby allowing drug 316 to elute or flow into the patient in a controlled manner. In an OFF state, drug flow is cease by closing apertures 314 via a reconfiguration of sleeve member 312 upon receiving the electrical stimulus so that apertures 314 are covered by outer sleeve member 310. This approach allows better control of the flow rate of a drug, with or without a particulate substance, to the patient.

In another embodiment, drug delivery arrangement 300 is incorporated into a pacing/sensing electrode lead head member that is implantable in a patient's heart. In this embodiment, drug delivery device 308 is disposed within the electrode lead head member and opens via an electrical stimulus received from the electrode lead body. This approach to drug delivery can replace a monolithic controlled release (MCR) device normally incorporated into electrode leads. MCR devices typically include a small sponge disposed at the end of the electrode lead that elutes a steroid to inhibit implant rejection. The use of drug delivery device 308 provides the capability of inhibiting tissue inflammation, thereby delaying or preventing the onset of implant rejection, by controlling the elution rate, quantity and release time of the steroid. Device 308 can be intermittently stimulated to open and close, thereby locally releasing the desired drug in a controlled manner.

In related embodiment, the electrode lead head member of drug delivery arrangement 300 can be similarly formed from a shape memory alloy with a series of apertures. Similar to the embodiment illustrated in FIGS. 3A and 3B, the electrode lead head member would include outer sleeve member 310 and an inner sleeve member 312 having apertures 314. Drug 316 elutes out of inner sleeve member 312 via apertures 314 once drug delivery device 308 is in an ON position in response to an electrical stimulation of inner sleeve member 312. In the ON state, the electrical stimulation of inner sleeve member 312 causes inner sleeve member 312 to elongate and expose apertures 314, thereby allowing drug 316 to elute or flow into the patient in a controlled manner. In an OFF state, drug flow is cease by closing apertures 314 via a reconfiguration of sleeve member 312 upon receiving the electrical stimulus so that apertures 314 are covered by outer sleeve member 310. According to an alternate embodiment, both inner sleeve member 312 and outer sleeve member 310 include apertures not directly opposed. When in the ON state, outer sleeve member 310 is physically reconfigured by the stimulus so that the apertures positioned along inner sleeve member 312 become aligned with the apertures positioned along outer sleeve member 310, enabling flow of the drug outward from the electrode head member. When in the OFF state, the apertures positioned along outer sleeve member 310 are covered by a portion of inner sleeve member 312 not having apertures and the apertures positioned along inner sleeve member 312 are covered by a portion of outer sleeve member 310 not having apertures, preventing flow of the drug outward from the electrode head member. Upon stimulating the electrode head member, the head member elongates and exposes the apertures, thereby releasing the drug stored within the head member. This approach prevents the formation of fibrosis around the apertures by intermittently releasing a steroid that inhibits tissue inflammation. The electrode head member can be easily placed against the surface of an internal body tissue, such as the myocardium of the heart, to increase the penetration of drug delivery to the body tissue. With this approach the drug is not diluted by local bodily fluids, because the drug is delivered directly to the body tissue or organ.

According to an embodiment of the present invention, the drug delivery system may include more than one valve arrangement as described above, so that two or more sets of apertures are positioned along various portions of the inner and outer sleeve members, longitudinally displaced relative to one another along a length of the inner and outer sleeve members, to form multiple sleeve valves that may act as surrogate valves in the case a primary valve becomes occluded.

Various modifications, equivalent processes, as well as numerous structures to which the present invention may be applicable will be readily apparent to those of skill in the art to which the present invention is directed upon review of the present specification. The claims are intended to cover such modifications and devices.

We claim:

1. A medical delivery system for delivering a fluid to a desired location within a body, comprising:
a first member comprised of a shape memory alloy and having an aperture;
a second member repositionable with respect to the first member;
a first fluid storage device, formed by at least one of the first member and the second member, containing the fluid; and
a power source operatively coupled to the first member, the first member being in a first state with respect to the second member when the power source does not apply power to the shape memory alloy of the first member and the first member being in a second state with respect to the second member when the power source applies power to the shape memory alloy of the first member; wherein in the second state, the first member elongates to expose the aperture to enable passage of the fluid outward from the first fluid storage device through the aperture.

2. The system of claim 1, further comprising a pressure sensing device communicatively coupled to the power source, the pressure sensing device adapted to sense pressure and generate a pressure feedback signal, wherein the power source delivers power to the first member in response to the pressure feedback signal.

3. The system of claim 1, wherein the second member is comprised of a shape memory alloy, and wherein the power source delivers power to the first member and the second member to reposition the first member relative to the second member to enable passage of the fluid outward from the first fluid storage device through the aperture.

4. The system of claim 1, wherein the second member includes a second aperture enabling passage of the fluid outward from the first fluid storage device through the second aperture in the second state, and wherein the first member prevents passage of the fluid through the second aperture and the second member prevents passage of fluid through the aperture of the first member when in the first state.

5. The system of claim 1, wherein the shape memory alloy includes titanium nitinol.

6. The system of claim 1, wherein the first member is adapted to be disposed within the second member.

7. The system of claim 1, further comprising:
a second fluid storage device storing the fluid; and
a fluid transfer device transferring the fluid from the second fluid storage device to the first fluid storage device, wherein the first member and the second member are in the first state during transfer of the fluid from the second fluid storage device to the first fluid storage device by the fluid transfer device.

8. A medical delivery system for delivering a fluid to a desired location within a body, comprising:
a first member comprised of a shape memory alloy and having an aperture;
a second member respositionable with respect to the first member;
a first fluid storage device, formed by at least one of the first member and the second member, containing the fluid;
a power source operatively coupled to the first member, the first member being in a first state with respect to the second member when the power source does not apply power to the shape memory alloy of the first member and the first member being in a second state with respect to the second member when the power source applies power to the shape memory alloy of the first member;
wherein in the second state, the first member elongates to expose the aperture to enable passage of the fluid outward from the first fluid storage device through the aperture; and
a pressure sensing device communicatively coupled to the power source, the pressure sensing device adapted to sense pressure and generate a pressure feedback signal, wherein the power source delivers power to the first member in response to the pressure feedback signal.

9. The system of claim 8, wherein the power source delivers power to the first member to reposition the first member relative to the second member to enable passage of the fluid outward from the first fluid storage device through the aperture.

10. The system of claim 9, wherein the first member is adapted to be disposed within the second member.

11. The system of claim 8, wherein the second member is comprised of a shape memory alloy, and wherein the power source delivers a stimulus to the first member and the second member to reposition the first member relative to the second member to enable passage of the fluid outward from the first fluid storage device through the aperture.

12. The system of claim 8, wherein the second member includes a second aperture enabling passage of the fluid outward from the first fluid storage device through the second aperture in the second state, and wherein the first member prevents passage of the fluid through the second aperture and the second member prevents passage of fluid through the aperture of the first member when in the first state.

13. The system of claim 8, wherein the shape memory alloy includes titanium nitinol.

14. The system of claim 8, wherein the pressure feedback signal corresponds to maintaining fluid pressure at the aperture at a predetermined flow rate.

15. The system of claim 8, further comprising:
a second fluid storage device storing the fluid; and
a fluid transfer device transferring the fluid from the second fluid storage device to the first fluid storage device, wherein the first member and the second member are in the first state during transfer of the fluid from the second fluid storage device to the first fluid storage device by the fluid transfer device.

16. A medical delivery system for delivering a fluid to a desired location within a body, comprising:
a first member comprised of a shape memory alloy and having an aperture;
a second member adapted to be positioned over the first member;
a first fluid storage device, formed by at least one of the first member and the second member, containing the fluid;
a power source operatively coupled a power source operatively coupled to the first member, the first member being in a first state with respect to the second member when the power source does not apply power to the shape memory alloy of the first member and the first member being in a second state with respect to the second member when the power source applies power to the shape memory alloy of the first member;
wherein in the second state, the first member elongates to expose the aperture to enable passage of the fluid outward from the first fluid storage device through the aperture;
a pressure sensing device communicatively coupled to the power source, the pressure sensing device adapted to sense pressure and generate a pressure feedback signal, the power source delivering power to the first member in response to the pressure feedback signal;
a second fluid storage device storing the fluid; and
a fluid transfer device transferring the fluid from the second fluid storage device to the first fluid storage device, wherein the first member and the second member are in the first state during transfer of the fluid from the second fluid storage device to the first fluid storage device by the fluid transfer device, wherein the pressure feedback signal corresponds to maintaining fluid pressure at the aperture at a predetermined flow rate.

17. A medical delivery system for delivering a fluid to a desired location within a body, comprising:
a first cylindrical member comprised of a shape memory alloy and formed by a first cylindrical member wall and having an aperture positioned along and extending through the first cylindrical member wall;
a second cylindrical member formed by a second cylindrical wall and having a diameter greater than the first cylindrical member, the first cylindrical member positioned within the second cylindrical member; and
a power source operatively coupled to the first cylindrical member, the first cylindrical member being in a first state with respect to the cylindrical member when the power source does not apply power to the shape memory alloy of the first cylindrical member and the first cylindrical member being in a second state with respect to the second cylindrical member when the power source applies power to the shape memory alloy of the first cylindrical member;
wherein the first cylindrical member is positioned within the second cylindrical member so that the second cylindrical member wall extends over a portion of the first cylindrical member wall including the aperture to prevent passage of the fluid through the aperture in the first state, and a second state wherein the first cylindrical member elongates within the second cylindrical member so that the second cylindrical member wall extends over a portion of the first cylindrical member wall that does not include the aperture to enable passage of the fluid through the aperture.

18. The system of claim 17, further comprising:
a fluid storage device storing the fluid; and
a fluid transfer device transferring the fluid from the fluid storage device to the first cylindrical member, wherein the first cylindrical member and the second cylindrical member are in the first state during transfer of the fluid from the fluid storage device to the first cylindrical member.

19. A medical delivery system for delivering a fluid to a desired location within a body, comprising:
   a first cylindrical member comprised of a shape memory alloy and formed by a first cylindrical member wall and having an aperture positioned along and extending through the first cylindrical member wall;
   a second cylindrical member formed by a second cylindrical wall and having a diameter greater than the first cylindrical member, the first cylindrical member positioned within the second cylindrical member;
   a power source operatively coupled to the first cylindrical member, the first cylindrical member being in a first state with respect to the cylindrical member when the power source does not apply power to the shape memory alloy of the first cylindrical member and the first cylindrical member being in a second state with respect to the second cylindrical member when the power source applies power to the shape memory alloy of the first cylindrical member;
   wherein the first cylindrical member is positioned within the second cylindrical member so that the second cylindrical member wall extends over a portion of the first cylindrical member wall including the aperture to prevent passage of the fluid through the aperture in the first state, and a second state wherein the first cylindrical member elongates within the second cylindrical member so that the second cylindrical member wall extends over a portion of the first cylindrical member wall that does not include the aperture to enable passage of the fluid through the aperture.

20. The system of claim 19, wherein the stimulus is one of an electrical stimulus, a magnetic stimulus, and a thermal stimulus.

21. The system of claim 19, wherein the first cylindrical member is adapted to be disposed within the second cylindrical member.

22. A medical delivery system for delivering a fluid to a desired location within a body, comprising:
   a first cylindrical member comprised of a shape memory alloy and formed by a first cylindrical member wall and having an aperture positioned along and extending through the first cylindrical member wall;
   a second cylindrical member formed by a second cylindrical wall and having a diameter greater than the first cylindrical member, the first cylindrical member positioned within the second cylindrical member;
   a power source operatively coupled to the first cylindrical member, the first cylindrical member being in a first state with respect to the cylindrical member when the power source does not apply power to the shape memory alloy of the first cylindrical member and the first cylindrical member being in a second state with respect to the second cylindrical member when the power source applies power to the shape memory alloy of the first cylindrical member;
   wherein the first cylindrical member is positioned within the second cylindrical member so that the second cylindrical member wall extends over a portion of the first cylindrical member wall including the aperture to prevent passage of the fluid through the aperture in the first state and a second state wherein the first cylindrical member elongates within the second cylindrical member so that the second cylindrical member wall extends over a portion of the first cylindrical member wall that does not include the aperture to enable passage of the fluid through the aperture.

\* \* \* \* \*